United States Patent [19]

Osterburg et al.

[11] Patent Number: 4,544,776
[45] Date of Patent: Oct. 1, 1985

[54] PROCESS FOR SEPARATING METHANOL FROM THE REACTION PRODUCTS OBTAINED IN THE ETHERIFICATION OF $C_4$ THROUGH $C_7$ ISOOLEFINS WITH METHANOL

[75] Inventors: Günther Osterburg, Duisburg; Milan Prezelj, Frankfurt am Main, both of Fed. Rep. of Germany

[73] Assignee: Deutsche Texaco Aktiengesellschaft, Hamburg, Fed. Rep. of Germany

[21] Appl. No.: 451,707

[22] Filed: Dec. 20, 1982

[30] Foreign Application Priority Data

Dec. 22, 1981 [DE] Fed. Rep. of Germany ....... 3150755

[51] Int. Cl.$^4$ .................. C07C 41/38; C07C 41/42
[52] U.S. Cl. .................. 568/697; 568/699; 568/913; 203/43; 203/71; 203/DIG. 6; 203/DIG. 19
[58] Field of Search .......... 203/38, DIG. 19, 43, 203/71, 99, DIG. 6; 568/918, 913, 697, 699; 585/809

[56] References Cited

U.S. PATENT DOCUMENTS

| 4,144,138 | 3/1979 | Rao et al. | 568/699 X |
| 4,302,298 | 11/1981 | Mikitenko et al. | 568/699 X |
| 4,324,924 | 4/1982 | Torck et al. | 568/699 X |
| 4,334,964 | 6/1982 | Prezelj et al. | 203/14 |

FOREIGN PATENT DOCUMENTS 1473263  5/1977  United Kingdom .

Primary Examiner—Wilbur Bascomb
Attorney, Agent, or Firm—Robert A. Kulason; Carl S. Seutter

[57] ABSTRACT

The reaction product from etherification of $C_4$-$C_7$ isoolefins with methanol in the presence of an acidic catalyst is washed with water in the presence of inert hydrocarbons thereby removing methanol and a part of the tertiary alcohol. The aqueous extract solution bottoms is distilled to separate methanol as overhead. Tertiary alcohols are withdrawn as a side stream from a tray of the distillation column with a high concentration thereof and fed into the washing column.

7 Claims, 2 Drawing Figures

PROCESS FOR SEPARATING METHANOL FROM THE REACTION PRODUCTS OBTAINED IN THE ETHERIFICATION OF C₄ THROUGH C₇ ISOOLEFINS WITH METHANOL

FIELD OF THE INVENTION

This invention relates to a process for splitting the reaction mixture obtained in the manufacture of asymmetrical ethers by reacting $C_4$–$C_7$ isolefins with methanol in the presence of an acidic catalyst, preferably an acidic cation exchange resin, and for separating the unreacted methanol by washing with water and subsequently separating the organic and aqueous phases.

BACKGROUND OF THE INVENTION

Preferably, the isoolefin-containing reaction feedstock originates from a light hydrocarbons cut obtained by pyrolysis or from a catalytic cracking unit. The reacting components are particularly isobutene and isopentene. The alcohol employed is preferably methanol. The ethers formed are particularly methyl-t-butyl ether (MTBE) and methyl-t-amyl ether (TAME) which are important motor fuel additives.

The process for producing the ethers and the splitting of the ether-containing reaction mixture by a washing stage directly following the reaction stage is the subject of DE-OS No. 25 47 380. This sequence of treatment steps, namely washing prior to distillative splitting, has the essential advantage of optional methanol dosage and complete removal of the alcohol in any case in a single step without the necessity of combining time-consuming azeotrope distillations which might require additional columns.

Using a suitably designed washing column, e.g. a conventional extraction column with five theoretical extracting stages (the methanol/water ratio being about 1:10 to 1:20) it is possible to extract from the reaction mixture all the alcohols formed including methanol and the by-product tertiary alcohols, particularly tert. butanol (TBA). The ethers, i.e. MTBE and others remain practically completely in the organic phase, because the presence of liquid phase unreacted hydrocarbons contained in the feedstock has a favorable effect on the ether distribution.

The aqueous extract thus obtained from the bottoms of the washing column contains besides water about 5 to 10% methanol, 0.5 to 1% MTBE, and 0.3 to 0.5% TBA. This mixture is subjected to atmospheric distillation in order to recover the methanol for the purpose of reuse.

In this distillation MTBE, removed overhead as an azeotrope with methanol, is recycled to the reactor, and does not cause any further difficulties in this connection.

Not so the tertiary alcohols and particularly TBA. In the distillation of the aqueous extract, this alcohol distills overhead as a water azeotrope and thus undesirably increases the water content in the methanol recycle. This water introduced with the recycle stream into the reactor causes the reaction course of the isobutene conversion to be shifted towards formation of TBA. An enrichment circuit with additional "snowball effect" would be closed by repeated extraction of the TBA in the water-washing step and subsequent recycling to the reactor, because no removal through the washed organic phase takes place. Such enrichment of TBA in the methanol cycle suppresses already, after a short operating time, the MTBE synthesis in the reactor and results in lower yield of MTBE.

DESCRIPTION OF THE PRIOR ART

U.S. Pat. No. 4,334,964 issued June 15, 1982 to Edeleanu Gmbh as assign of Milan Prezelj, Gunter Osterburg, and Joachim E. Putz discloses a process for separating the reaction products obtained from etherifying lower isoolefins with methanol.

It is one object of this invention to provide an improved process for separating the product mixture obtained in the synthesis of tert. alkyl ethers by employing a water-washing unit directly succeeding the reactor, the aqueous extract from this unit then being treated by distillation. The methanol obtained in the aqueous extract from the washing column is separated as completely as possible from the tertiary alcohols and is reused. Other objects will be apparent to those skilled in the art.

STATEMENT OF THE INVENTION

In accordance with certain of its aspects, this invention is directed to a process for separating methanol from the reaction products of the etherification of $C_4$–$C_7$ isoolefins with methanol which comprises washing the etherification reaction products at 20° C.–60° C., immediately after etherification, with water in the presence of inert hydrocarbons and a recycle stream containing a high concentration of tertiary alcohol thereby forming (i) a raffinate and (ii) an aqueous extract bottoms containing alcohols including methanol and tertiary alcohol in said washing operation;

maintaining a methanol:water ratio of 1:1.5 to 1:10 in said washing operation;

passing said aqueous extract bottoms to a distillation column;

distilling said aqueous extract bottoms in said distillation column thereby forming distillation overhead containing methanol;

withdrawing a side stream containing tertiary alcohols from a tray of said distillation column containing a high concentration of tertiary alcohol; and passing said withdrawn side stream as said recycle stream to said washing operation.

DESCRIPTION OF THE INVENTION

The hydrocarbon charge to the process of this invention preferably includes isoolefin streams containing a content of isobutene and isopentene together with substantial quantities of inert hydrocarbons. Typical of such streams are light hydrocarbon streams recovered from cracking or from pyrolysis.

Charge also includes a water-soluble alcohol, typified by methanol. A recycle stream of methanol, containing small quantities of product ether, is preferably also admitted as charge to etherification.

Etherfication is carried out in liquid phase in the presence of acid etherification catalyst preferably an acid resin catalyst such as the Amberlyst 15 brand of sulfonated styrene-divinyl benzene copolymer. Etherification proceeds typically at temperature of 70° C. at pressure of 12 bar. Effluent contains product methyl t-butyl ether in an excess of inert hydrocarbon; and the solution contains methanol, t-butyl alcohol, and unreacted olefin.

In practice of the invention, the effluent is combined with a recycle stream of t-butyl alcohol (which also contains methanol and water) and the combined stream is passed to a water washing operation wherein it is counter currently contacted with water. Water washing is carried out at a lower temperature than etherification e.g. typically 40° C. and at a pressure (e.g. 10–12 Bar) sufficient to keep the hydrocarbon in liquid phase. Overhead raffinate from washing, containing principally inert hydrocarbons plus product ether together with lesser amounts of unreacted isoolefin and tertiary alcohol, is passed to distillation from which is recovered overhead containing inert hydrocarbon plus small quantities of water and unreacted isoolefins and bottoms containing desired product ether plus small quantities of tertiary alcohol.

The extract bottoms from the water-washing operation contain water and methanol plus small quantities of tertiary alcohol plus product ether. This stream is passed to a methanol distillation operation.

Methanol distillation operation is controlled (by regulating the reflux ratio) to give an overhead which is substantially methanol containing a small quantity of product ether—but which is essentially free of tertiary alcohol and water.

There is withdrawn from the methanol distillation column, a few trays above the point at which the extract bottoms stream is admitted thereto, a side stream having a high concentration of tertiary alcohol. The preferred tray may be that in the rectification section of the column which contains the highest concentration of tertiary alcohol. This withdrawn side stream, contains tertiary alcohol, methanol, and water; it is recycled to the water washing operation.

Bottoms from the methanol distillation column containing essentially water is recirculated to the top of the water-washing operation. A portion of this recycle water may be drawn off; and additional water may be added as necessary.

Thus the process of this invention for separating methanol from the reaction products obtained in a reactor in the etherification of $C_4$ through $C_7$ isoolefins with methanol may be carried out by washing reactor effluent with water directly following the reactor and in the presence of liquid inert hydrocarbons, a portion of the alcohol which contains methanol and tertiary alcohols being extracted with water in an aqueous extract solution, the aqueous extract solution (the bottoms extract from the washing column) being transferred therefrom to a distillation column in which the alcohols and water are separated by distillation. The process may be particularly characterized by extracting the reactor effluent (containing methanol) with water at a methanol/water ratio of 1:1.5 to 1:10 at a temperature of 20° C. to 60° C., preferably at a methanol/water ratio of 1:2 to 1:8, particularly 1:2 to 1:5 and a temperature of 40° C. to 50° C. The aqueous extract thus obtained is then distilled in order to recover methanol overhead from the methanol distillation column. Tertiary alcohols are withdrawn as a side stream from a tray with a high concentration of tertiary alcohols and the side stream is recycled to the washing column.

Thus, in the distillation of the aqueous extract removed from the washing column, the tertiary alcohols are discharged through a lateral outlet from the methanol/water column. A control device regulates the amount removed at the lateral outlet so that virtually no further tertiary alcohol leaves the column overhead. The portion removed through the lateral outlet of the water/alcohol separating column from a tray having a high concentration of tertiary alcohols also contains besides the tertiary alcohols, particularly TBA, considerable amounts of methanol. A typical composition for instance may contain 40% TBA, 50% methanol, and 10% water. This amount of methanol may amount to up to 20% of the total methanol recovered from the reaction mixture in the washing section.

Such methanol quantities cannot get lost as a by-product if a production unit is to be economically operated. It may be possible to dispose of this stream by incineration as a slop or admixed to the MTBE product, but either alternative is uneconomical or involves an undesired deterioration of the MTBE finished product quality. According to the present invention, this stream withdrawn from the methanol/water column is recycled to the washing column.

According to the present invention, the methanol is quantitatively extracted from the reaction mixture of the ether synthesis, whereas the tertiary alcohol is only partly extracted therefrom in accordance with its concentration in the reaction mixture and the distribution factor predetermined by the extraction temperature, employing a suitably designed washing column, particularly a non-pulsed sieve tray extraction column, and a methanol/water ratio of down to 1:2. The unextracted tertiary alcohol remains in the MTBE/hydrocarbons phase and leaves the process as a component of the MTBE product.

It is not necessary to treat the side stream containing methanol and water as well as the tertiary alcohols which is to be withdrawn from the methanol/water separating column in a second distillation column. On the contrary, this side stream can be surprisingly recycled to the washing column. Usually, it is simply admixed with the reactor effluent mixture.

By recycling the side stream, the concentration of tertiary alcohols in the MTBE/hydrocarbons mixture leaving the washing column increases. This action of concentration increase continues until the amount of tertiary alcohols contained in the MTBE/hydrocarbons mixture at the head of the washing column is equal to the amount formed as a by-product in the etherification reaction and entering the washing column together with the other reaction products. Hence with a constant amount of tertiary alcohols and water, a constant circulation of tertiary alcohols is established between extractor and methanol column. If the amount of TBA formed in the synthesis increases or decreases, or if the amount of wash water changes, the TBA distribution and thus TBA circulation will change accordingly.

A high water supply relative to the raffinate, is undesirable in operation of the process of the present invention, because with a higher amount of water more TBA is extracted. The removal through the raffinate phase thus becomes more and more uneconomical and finally no longer tolerable. A limitation to a minimum raffinate/water ratio of 2:1 is realistic for tertiary butyl alcohol (TBA) and physicaly grounded regardless of the conditions of the methanol extraction. The maximum raffinate/water ratio is not limited for the practical applicability of the present process, because with little water only little TBA is extracted. For the determination of a preferred upper threshold of the ratio in the MTBE process, it is necessary to consider the isobutene content of the charge a $C_4$-cut which can be economically used and treated in a MTBA synthesis. Thus, the conversion of a $C_4$-cut with an isobutene content of 12% or 7% at a conversion of 95% and a methanol excess of 20 mole % and a methanol/water ratio of 1:1.5 yields a raffinate/water ratio of 55:1 or 87:1, i.e. only an unrealistically low isobutene content may further increase the raffinate/water ratio. Hence, as the upper limit for the raffinate/water ratio 80:1, preferably 60:1, can be stated for practical reasons.

Like the described single-stage process for producing MTBE the process of the invention for splitting the reaction mixture can be employed in a further embodiment in a two-stage MTBE-process as for instance disclosed in DE-AS No. 2706465.

In a two-stage process the mixture leaving the first reactor is led to a distillation column from which unreacted hydrocarbons are removed overhead. In order to perform the conversion of the residual isoolefin contained in the hydrocarbon stream, this overhead is charged to a second reactor to which fresh methanol is admitted. The hydrocarbon removed overhead from the distillation column contains small amounts of azeotrope methanol (2-3%). As bottoms from the column, a mixture of MTBE, tertiary alcohols, and the remaining unreacted methanol is obtained. In order to separate alcohol and ether this mixture is charged to the water-operated extraction column after being combined with the hydrocarbons-rich product stream from the second reactor. It is known that the presence of liquid hydrocarbons in the washing operation reduces the transfer of MTBE into the aqueous phase and provides for the recovery of an absolutely methanol-free ether product regardless of the amounts of methanol charged to the reactor stages. Like in the single-stage MTBE processes, the distillative splitting of the aqueous phase is performed according to this invention, a side stream being removed and recycled to the washing section.

Also in this case of the two-stage MTBE synthesis, the process of the invention allows a residueless recycling of the unconverted methanol to the synthesis process.

DESCRIPTION OF THE DRAWINGS

In the following, the process of the invention relating to the production of MTBE is described by the FIGS. 1 and 2 of the drawing.

DESCRIPTION OF PREFERRED EMBODIMENTS

Figure 1:
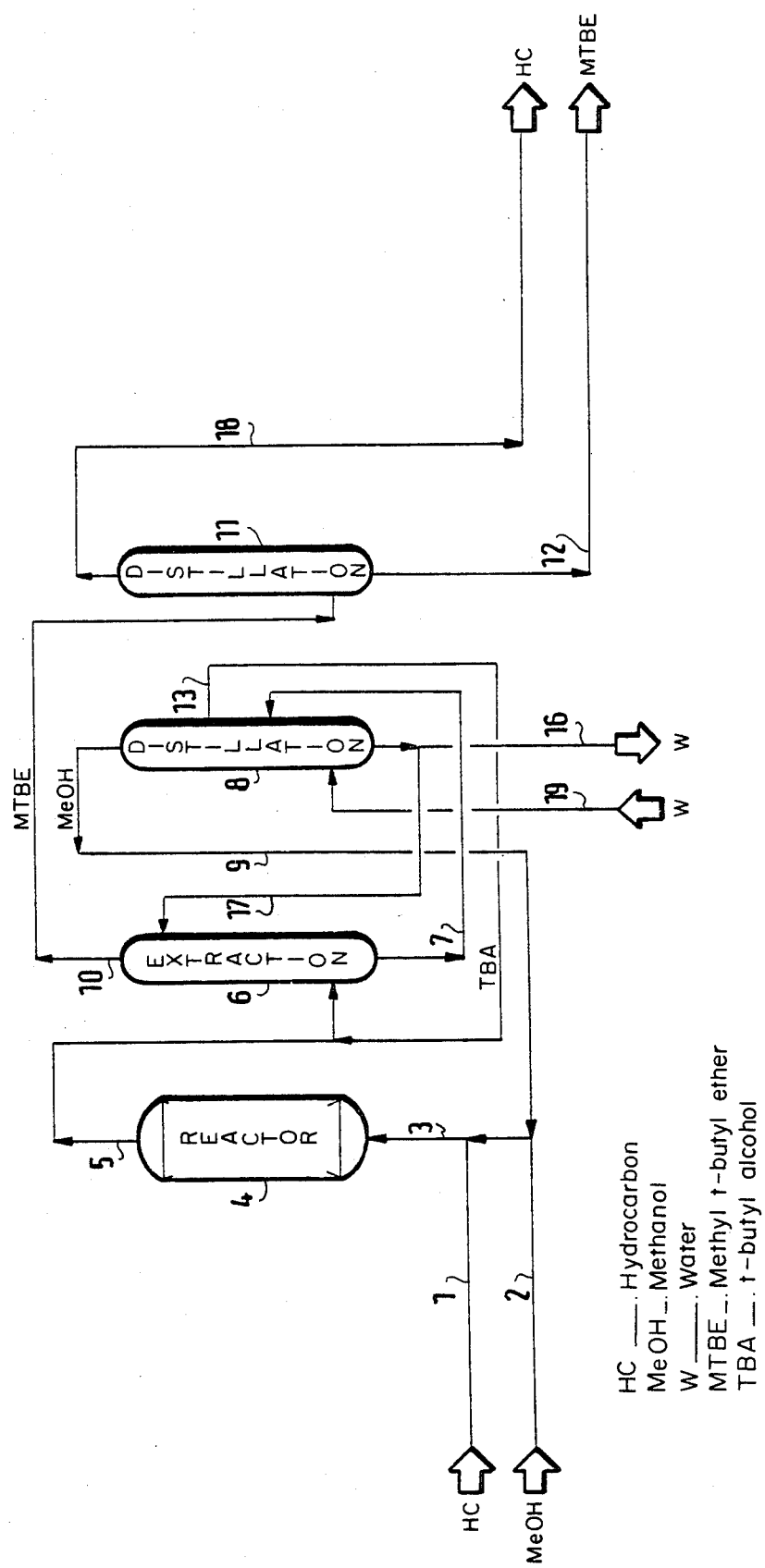
FIG. 1 illustrates the single-stage process.
Figure 2:
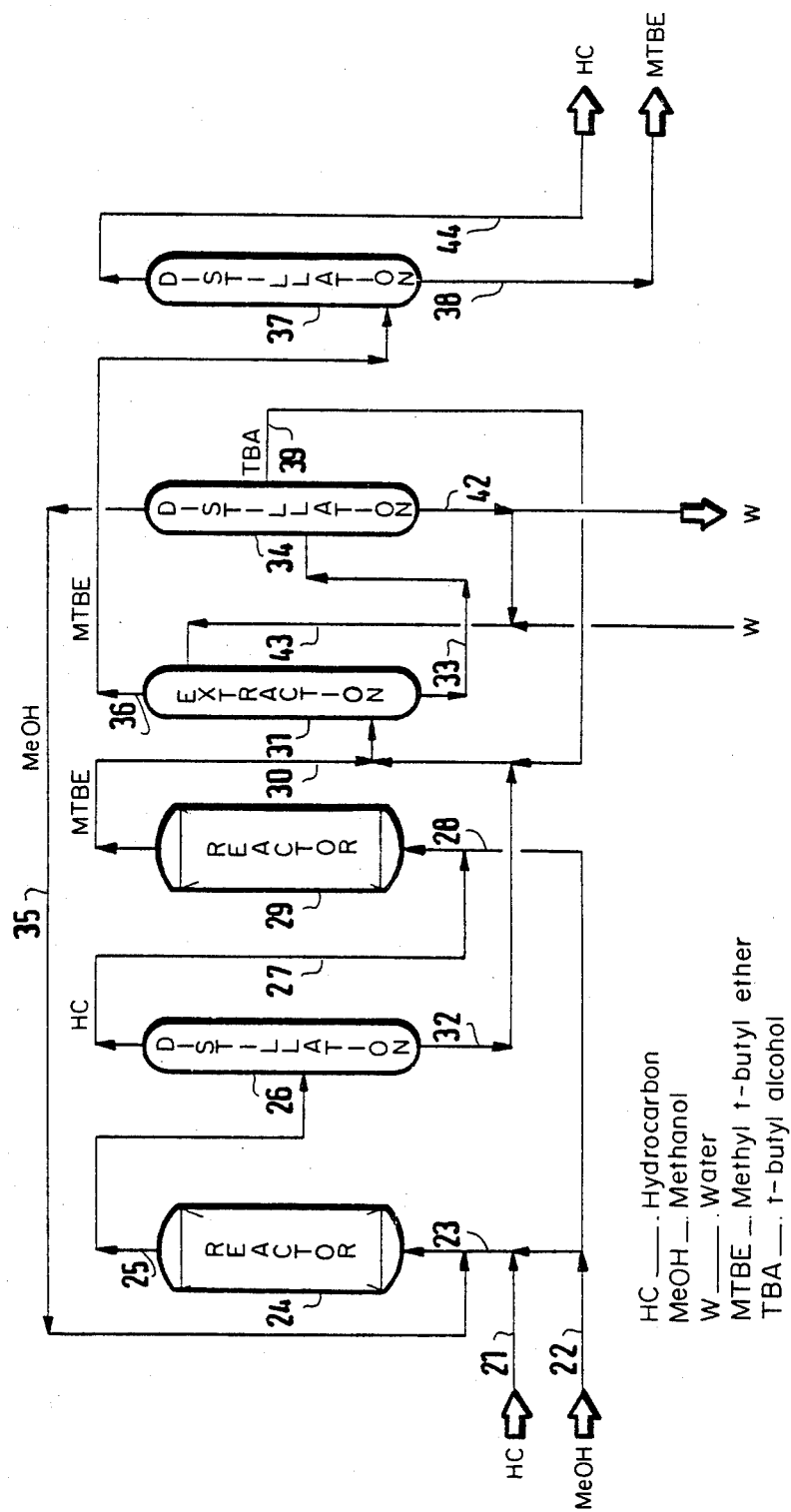
FIG. 2 illustrates the two-stage process.

Single Stage Process According to FIG. 1

An isobutene-containing $C_4$-hydrocarbons stream from line 1, fresh methanol from line 2, and a MTBE-containing methanol recycle stream from line 9 are jointly charged through line 3 to reactor 4. The reaction mixture leaving reactor 4 through line 5 is led together with the TBA-containing side stream from line 13 to extraction column 6 operated under pressure. In this extraction column the methanol is quantitatively removed, by washing with water, from the reaction product is countercurrent operation.

The water extract contains the total amount of methanol at a concentration of about 20% plus about 1% MTBE; and the TBA portion which is soluble under extraction conditions is recovered as bottoms from extraction column 6. This wash water bottoms is led through line 7 to the methanol/water distillation column. In this column, the methanol is distilled overhead at normal pressure together with the MTBE contained in the wash water and is condensed and recycled, as a methanol recycle stream, through line 9 to the reactor. In the methanol/water separation, the TBA accumulates in distillation column 8 so that from a suitable tray of the column, a TBA stream with a high TBA concentration can be withdrawn under control as a side stream which is transferred through line 13 together with the reaction product from line 5 to extraction column 6. The typical composition of such a TBA side stream is about 40% TBA, 50% methanol, and 10% water. The alcohol-free and MTBE-free wash water is directly returned as bottoms from distillation column 8 through line 17 to extraction column 6. Water can be withdrawn through line 16. Additional water, if needed, may be admitted through line 19.

By recycling the TBA side stream from the methanol/water separating column 8 to extraction column 6, the total amount of TBA formed in the reactor (by reacting water with isobutene) is charged together with the MTBE also formed there and with the unreacted or inert hydrocarbons as a raffinate phase from the extraction column, through line 10 to distillation column 11. In distillation column 11 the hydrocarbons and MTBE are separated. At the head of this distillation column a $C_4$-cut is withdrawn which is substantially free of methanol, TBA and MTBE; and this cut is withdrawn through line 18. As bottoms from column 11, methanol-free MTBE is obtained together with tertiary butyl alcohol (TBA). These products are removed through line 12.

TWO-STAGE PROCESS ACCORDING TO FIG. 2

An isobutene-containing $C_4$-hydrocarbons stream from line 21, fresh methanol from line 22, and a MTBE-containing methanol recycle stream from line 35 are jointly fed through line 23 to reactor 24. The reaction mixture leaving reactor 24 through line 25 is led to distillation column 26. The overhead product from distillation column 26, a $C_4$-hydrocarbons mixture with a residual content of unreacted isobutene, is withdrawn through line 27 and led together with fresh methanol from line 28 to reactor 29 where the residual isobutene is converted to methyl t-butyl ether. The reaction mixture composed of unconverted $C_4$-hydrocarbons, ether, and alcohol leaving reactor 29 through line 30 is led (together with the TBA-containing side stream from line 39 and the bottoms from distillation column 26 removed through line 32) to the lower section of extraction column 31 operated under pressure. In extraction column 31, the methanol is quantitatively washed out with water in countercurrent operation.

The wash water, withdrawn through line 33, contains water plus about 20 %wt. methanol, about 1 %wt. MTBE, and the TBA components soluble under extraction conditions. This wash water is transferred through line 33 to distillation column 34 where the methanol is removed overhead and charged as a methanol recycle stream through line 35 and line 23 to reactor 24 in order to reparticipate in the reaction. MTBE leaves extraction column 31 overhead as raffinate through line 36 together with the hydrocarbons components and flows through this line to distillation column 37 where the MTBE is recovered as bottoms discharged through line 38. From a suitable tray of distillation column 34, located several trays above the entrance of line 33 to the column and having a high TBA concentration, a TBA-containing side stream is withdrawn through line 39 and charged together with the reaction products from lines 30 and 32 to extraction column 31.

The typical composition of the side stream is about 40 %wt. TBA, about 50 %wt. MeOH, and about 10 %wt. $H_2O$. The water obtained as bottoms from distillation column 34 is discharged through line 42 or transferred through line 43 to washing column 31.

The vapor mixture leaving column 37 overhead contains the portion of the nonconvertible components of the hydrocarbons mixture and leaves the unit through line 44. Bottoms from column 37, methanol-free MTBE, is discharged together with TBA through line 38.

DESCRIPTION OF SPECIFIC EMBODIMENT

Practice of the process of this invention will be apparent to those skilled in the art from inspection of the following illustrative examples wherein all parts are parts by weight unless otherwise spelled out.

The following examples illustrate the invention:

EXAMPLE 1

34,618 parts of a $C_4$-hydrocarbons stream having the following composition:

TABLE

| Components | Parts |
|---|---|
| Isobutane | 311 |
| n-Butane | 2,041 |
| Butene-1 | 4,671 |
| cis-Butene-2 | 1,765 |
| trans-Butene-2 | 2,699 |
| Isobutene | 10,380 |
| 1,3-Butadiene | 12,733 |
| water | 18 | were charged through line 1 together with 5,680 parts of fresh methanol from line 2 and 1,133 parts of methanol with 60 parts of MTBE from line 9 to reactor 4 wherein isobutene and methanol reacted in the presence of Amberlyst 15 catalyst to form MTBE.

The conversion in the reactor took place at 70° C. and 12 bar. The isobutene conversion was 96%. The unconverted hydrocarbons left the reactor unchanged. The methanol excess was 20 mole %. From 18 parts of the water (about 0.05%) contained in the reactor feedstock, 74 parts of TBA were formed in the reactor by conversion with 56 parts of isobutene corresponding to 0.6% of the isobutene feed.

The reaction mixture leaving reactor 4 through line 5 had the following composition:

TABLE

| Components | Parts |
|---|---|
| Inert hydrocarbons | 24,190 |
| Isobutene | 415 |
| Methanol | 1,133 |
| TBA | 74 |
| MTBE | 15,631 |
| Crotyl ethers | 48 |

In extraction column 6, this product stream and the product stream from line 13 (15 parts of TBA, 21 parts of methanol, and 4 parts of water) were washed in countercurrent operation with 4728 parts of water at 40° C.

The methanol/water ratio in the washing column was about 1:4. By an excess pressure of 12 bar, the hydrocarbons were kept liquid. The methanol dissolved quantitatively in the aqueous extract phase. MTBE, in the presence of hydrocarbons, dissolved to about 1% in the extract phase. Under these extraction conditions, TBA dissolved only to a limited extent in the extract phase, so that of the total of 89 parts of TBA charged to the extraction column, 74 parts of TBA were discharged with the raffinate stream. The raffinate consisted of:

TABLE

| Components | Parts |
|---|---|
| crotyl ethers | 48 |
| inert hydrocarbons | 24,190 |
| isobutene | 415 |
| MTBE | 15,571 |
| TBA | 74 |
| water | 60 |
| raffinate | 40,358 |
| (raffinate:water = 8.5:1) | | and was separated in distillation column 11. As overhead from distillation column 11, there are recovered

TABLE

| Components | Parts |
|---|---|
| inert hydrocarbons | 24,220 |
| isobutene | 415 |
| water | 60 |

The insoluble water was separated and discharged.

As bottoms from column 11, 15,571 parts of MTBE, 74 parts of TBA and 48 parts of crotyl ethers were withdrawn.

The extract phase contains

TABLE

| Components | Parts |
|---|---|
| water | 4,672 |
| methanol | 1,154 |
| MTBE | 60 |
| TBA | 15 |

This extract phase was charged to methanol/water separating column 8. The soluble organic components were stripped from the water by distillation so that as overhead from the column, 1,133 parts of methanol and 60 parts of MTBE were removed and recycled to the reactor 4.

From the tray with the highest TBA concentration, tray 28, a side stream containing TBA which was with the extract phase admitted to separating column 8 (and enriched as compared to methanol and water) is withdrawn and returned to extraction column 6.

The quantity of the side stream was:

TABLE

| Components | Parts |
|---|---|
| TBA | 15 |
| methanol | 21 |
| water | 4 |

Hence, from a total of 89 parts of TBA 15 parts = 17% were extracted, withdrawn, and returned to extraction column 6.

EXAMPLE II 34,620 parts of a $C_4$-hydrocarbons stream from line 1 with the following composition

| Isobutane | 311 |
|---|---|
| n-Butane | 2,041 |
| Butene-1 | 4,671 |
| cis-Butene-2 | 1,765 |
| trans-Butene-2 | 2,699 |

-continued

| Components | Parts |
| --- | --- |
| Isobutene | 10,380 |
| 1,3-Butadiene | 12,733 |
| water | 20 | were charged to reactor 4 together with 5,767 parts of fresh methanol from line 2 and 4,590 parts of methanol plus 230 parts of MTBE from line 9.

The conversion in the reactor took place at 70° C. and 12 bar. The isobutene conversion was 97.3%. The methanol excess was 80 mole %.

From 20 parts of the water (approx. 0.05%) contained in the reactor feedstock and 62 parts of isobutene corresponding to 0.6% of the isobutene feed, 82 parts of TBA were formed.

The reactor effluent had the following composition:

TABLE

| Components | Parts |
| --- | --- |
| Inert hydrocarbons | 24,171 |
| Isobutene | 277 |
| Methanol | 4,590 |
| TBA | 82 |
| MTBE | 16,009 |
| Crotyl ethers | 78 |

This stream was combined with the TBA side stream from line 13 (123 parts of TBA, 176 parts of methanol, and 33 parts of water) and the combined stream washed with 18,387 parts of water at 40° C. in countercurrent operation.

The methanol/water ratio was 1:4. The methanol was washed out quantitatively. MTBE dissolved at 1% in the extract phase. TBA dissolved to a limited extent according to the extraction conditions so that of the 205 parts of TBA charged to the extraction column, 82 parts of TBA were withdrawn in the raffinate stream.

Composition of the raffinate phase:

TABLE

| Components | Parts |
| --- | --- |
| crotyl ethers | 78 |
| inert hydrocarbons | 24,171 |
| isobutene | 277 |
| MTBE | 15,779 |
| TBA | 82 |
| water | 60 |
| raffinate | 40,447 |
| (raffinate:water = 2.2:1) | |

As overhead from distillation column 11, the following was removed:

TABLE

| Components | Parts |
| --- | --- |
| inert hydrocarbons | 24,220 |
| isobutene | 277 |
| water | 60 |

The water was separated therefrom and discharged.

15,779 parts of MTBE, 82 parts of TBA and 78 parts of crotyl ethers were withdrawn as bottoms from column 11.

| | |
| --- | --- |
| 18,360 | parts of water |
| 4,766 | parts of methanol |
| 230 | parts of MTBE |
| 123 | parts of TBA | were charged as an extract phase through line 7 to separating column 8. From this column, 4,590 parts of methanol and 230 parts of MTBE were removed as a condensed overhead product and were returned through line 9 to the reactor.

From tray 28 of column 8, a TBA side stream with 123 parts of TBA, 176 parts of methanol, and 33 parts of water were removed and returned to extraction column 6.

Thus, of a total of 205 parts of TBA, 123 parts=60% were extracted, removed, and returned.

EXAMPLE III 123,948 parts of a $C_4$-hydrocarbons stream from line 1 with the following composition

TABLE

| Components | Parts |
| --- | --- |
| $C_3$—Hydrocarbons | 3,448 |
| Isobutane | 35,749 |
| n-Butane | 16,462 |
| Butene-1 | 12,753 |
| cis-Butene-2 | 9,837 |
| trans-Butene-2 | 14,710 |
| Isobutene | 18,003 |
| $C_5$—Hydrocarbons (pentanes, pentenes) | 12,924 |
| water | 62 | were led to reactor 4 together with 10,289 parts of fresh methanol and 8,231 parts of methanol+390 parts of MTBE from line 9. The conversion in the reactor took place at 70° C. and 12 bar. The isobutene conversion was 97%. The methanol excess was 80%.

From 62 parts (approx. 0.05%) of the water contained in the reactor feedstock and 193 parts of isobutene, corresponding to 1.1% of the isobutene feed, 255 parts of TBA were formed.

The reactor effluent has the following composition:

TABLE

| Components | Parts |
| --- | --- |
| inert hydrocarbons | 92,959 |
| isobutene | 540 |
| C—5 hydrocarbons (pentanes, pentenes) | 12,006 |
| methanol | 8,231 |
| TBA | 255 |
| MTBE | 27,529 |
| tame | 1,338 |

This stream was washed in countercurrent operation together with the TBA side stream from line 13 (127 parts of TBA, 182 parts of methanol, and 34 parts of water) with 33,652 parts of water at 40° C.

The methanol/water ratio was 1:4. The methanol was washed out quantitatively. MTBE dissolved at 1% in the extract phase. TBA dissolved to a limited extent according to the extraction conditions. Of 382 parts of TBA charged to the extraction column, 255 parts of TBA were removed with the raffinate stream.

Composition of the raffinate phase

TABLE

| Components | Parts |
| --- | --- |
| inert hydrocarbons | 92,959 |
| isobutene | 540 |
| C—5 hydrocarbons (pentanes, pentenes) | 12,006 |
| TBA | 255 |
| water | 132 |
| Tame | 1,338 |
| MTBE | 27,139 |
| raffinate | 134,369 |

TABLE-continued

| Components | Parts |
| --- | --- |
| (raffinate:water = 4.0:1) | |

From the head of distillation column 11 were withdrawn, through line 18

TABLE

| Components | Parts |
| --- | --- |
| inert hydrocarbons(incl. C—5 hydrocarbon) | 104,819 |
| isobutene | 540 |
| water | 132 |

The water was separated and discharged.

27,139 parts of MTBE, 255 parts of TBA, 1,338 parts of TAME and 146 parts of C-5 hydrocarbons were obtained as bottoms in line 12.

TABLE

| Components | Parts |
| --- | --- |
| water | 33,554 |
| methanol | 8,413 |
| MTBE | 390 |
| TBA | 127 | were charged as an extract phase to separating column 8. From this column, 8,231 parts of methanol and 390 parts of MTBE were withdrawn as a condensed overhead product and were returned through line 9 to the reactor.

From tray 28 of column 8, a TBA side stream (containing 127 parts of TBA, 182 parts of methanol, and 34 parts of water) was withdrawn and returned to extraction column 6 through line 13.

Hence a total of 382 parts of TBA, 127 parts=33% were extracted, removed and recycled.

EXAMPLE IV 34,620 parts of a $C_4$-hydrocarbons stream from line 1 with the following composition:

TABLE

| Components | Parts |
| --- | --- |
| Isobutane | 311 |
| n-Butane | 2,041 |
| Butene-1 | 4,671 |
| cis-Butene-2 | 1,765 |
| trans-Butene-2 | 2,699 |
| Isobutene | 10,380 |
| 1,3-Butadiene | 12,733 |
| Water | 20 | were charged to reactor 4 together with 5,767 parts of fresh methanol and 4,590 parts of methanol and 141 parts of MTBE form line 9.

The conversion in the reactor took place at 70° C. and 12 bar. The isobutene conversion was 97.3%. The methanol excess was 80% by mole.

From 20 parts of the water (approx. 0.05%) contained in the reactor feedstock and 62 parts of isobutene corresponding to 0.6% of the isobutene feed, 82 parts of TBA were formed.

The reactor effluent had the following composition:

TABLE

| Components | Parts |
| --- | --- |
| Inert hydrocarbons | 24,171 |
| Isobutene | 277 |

TABLE-continued

| Components | Parts |
| --- | --- |
| Methanol | 4,590 |
| TBA | 82 |
| MTBE | 15,920 |
| Crotyl ethers | 78 |

This stream was washed in counter current operation 6 together with the TBA side stream from line 13 (38 parts of TBA, 54 parts of methanol, and 10 parts of water) with 9,300 parts of water at 40° C.

The methanol/water ratio was 1:2. The methanol was washed out quantitatively. MTBE dissolved at 1% in the extract phase. TBA dissolved to a limited extent according to the extraction conditions so that of the 120 parts of TBA charged to the extraction column 82 parts of TBA were discharged with the raffinate stream.

Composition of the raffinate phase:

TABLE

| Components | Parts |
| --- | --- |
| Crotyl ethers | 78 |
| inert hydrocarbons | 24,171 |
| isobutene | 277 |
| MTBE | 15,779 |
| TBA | 82 |
| water | 60 |
| raffinate | 40,447 |
| (raffinate:water = 4.3:1) | |

As overhead from distillation column 11

TABLE

| Components | Parts |
| --- | --- |
| inert hydrocarbons | 24,220 |
| isobutene | 277 |
| water | 60 | were withdrawn; the water was separated and discharged. 15,779 parts of MTBE, and 82 parts of TBA, and 78 parts of crotyl ethers were removed as bottoms in line 12.

| | |
| --- | --- |
| 9,240 | parts of water |
| 4,644 | parts of methanol |
| 141 | parts of MTBE |
| 38 | parts of TBA | were charged as an extract phase to separating column 8. From this column, 4,590 parts of methanol and 141 parts of MTBE were removed as a condensed overhead product and were returned through line 9 to the reactor.

From tray 28 of column 8, a TBA side stream with 38 parts of TBA, 54 parts of methanol, and 10 parts of water was withdrawn and returned to extraction column 6.

Thus, of a total of 120 parts of TBA 38 parts32 32% were extracted, removed and recycled.

Although this invention has been illustrated by reference to specific embodiments, it will be apparent to those skilled in the art that various changes and modifications may be made which clearly fall within the scope of this invention.

We claim:

1. The process for separating methanol from the reaction products of the etherification of $C_4$–$C_7$ isoolefins with methanol which comprises washing the etherification reaction products at 20° C.–60° C., immediately after etherification, with water in the presence of inert hydrocarbons and a recycle stream containing a high concentration of a tertiary alcohol thereby forming (i) a raffinate and (ii) an aqueous extract bottoms containing alcohols including methanol and the tertiary alcohol in said washing operation;

maintaining a methanol:water weight ratio of 1:1.5 to 1:10 in said washing operation;

passing said aqueous extract bottoms to a distillation column;

distilling said aqueous extract bottoms in said distillation column thereby forming distillation overhead containing methanol;

withdrawing a side stream containing the tertiary alcohol from a tray of said distillation column containing a high concentration of the tertiary alcohol; and passing said withdrawn side stream as said recycle stream to said washing operation.

2. The process for separating methanol from the reaction products of the etherification of $C_4$–$C_7$ isoolefins with methanol as claimed in claim 1 wherein during the washing operation the weight ratio of raffinate to water is maintained at a level of at least 2:1.

3. The process for separating methanol from the reaction products of the etherification of $C_4$–$C_7$ isoolefins with methanol as claimed in claim 1 wherein the methanol:water weight ratio is 1:2 to 1:8.

4. The process for separating methanol from the reaction products of the etherification of $C_4$–$C_7$ isoolefins with methanol as claimed in claim 1 wherein the methanol:water weight ratio is 1:2 to 1:5.

5. The process for separating methanol from the reaction products of the etherification of $C_4$–$C_7$ isoolefins with methanol as claimed in claim 1 wherein the temperature in the washing operation is 40° C.–50° C.

6. The process for separating methanol from the reaction products of the etherification of $C_4$–$C_7$ isoolefins with methanol as claimed in claim 1 wherein the distillation overhead from said distillation operation contains methanol and is substantially free of the tertiary alcohol.

7. The process for separating methanol from the reaction products of the etherification of $C_4$–$C_7$ isoolefins with methanol which comprises distilling the etherification reaction products from a first stage etherification operation thereby separating overhead containing unreacted hydrocarbons including $C_4$–$C_7$ isoolefins and bottoms containing product ether and alcohols including methanol and a tertiary alcohol;

reacting said overhead with methanol in a second stage etherification operation thereby forming second stage product stream containing product ether and alcohols including methanol and a tertiary alcohol;

combining (i) said bottoms containing product ether and alcohols including methanol and the tertiary alcohol, (ii) said second stage product stream containing product ether and alcohols including methanol and the tertiary alcohol, and (iii) a recycle stream containing a high concentration of the tertiary alcohol thereby forming a combined stream;

washing said combined stream at 20° C.–60° C. with water in the presence of inert hydrocarbons thereby forming (i) a raffinate and (ii) an aqueous extract bottoms containing alcohols including methanol and the tertiary alcohol in said washing operation;

distilling said aqueous extract bottoms in a distillation column thereby forming (i) overhead containing methanol and (ii) bottoms containing water;

recovering said overhead containing methanol;

withdrawing a side stream containing the tertiary alcohol from a tray of said distillation column containing a high concentration of the tertiary alcohol; and passing said withdrawn side stream, as said recycle stream, to said combining operation.

* * * * *